(12) United States Patent
Murali et al.

(10) Patent No.: US 7,932,086 B2
(45) Date of Patent: Apr. 26, 2011

(54) **COMMERCIALLY VIABLE PROCESS FOR IN VITRO MASS CULTURE OF *JATROPHA CURCAS***

(75) Inventors: Krishnapuram Sreenivasachar Murali, Navi Mumbai (IN); Monali Patil, Navi Mumbai (IN); Ghanshyam Maurya, Navi Mumbai (IN)

(73) Assignee: Reliance Life Sciences Pvt. Ltd., Navi-Mumbai (IN)

( * ) Notice: Subject to any disclaimer, the term of this patent is extended or adjusted under 35 U.S.C. 154(b) by 492 days.

(21) Appl. No.: 11/706,608

(22) Filed: Feb. 14, 2007

(65) Prior Publication Data

US 2008/0196121 A1 Aug. 14, 2008

(51) Int. Cl.
*A01H 5/00* (2006.01)
(52) U.S. Cl. .......................................... 435/420
(58) Field of Classification Search ................... 435/420
See application file for complete search history.

(56) References Cited

FOREIGN PATENT DOCUMENTS

CN 1799340 * 7/2006

OTHER PUBLICATIONS

Sardana et al. In vitro plantlet formation and micropropagation of *Jatropha curcase* Ad. Plant. Sci. 11(2) 167-169 (1998).*
Rajore et al. Efficient Plant Regneration vio Shoot Tip Explants in *Jatropha curcase*. J. Plant Biochem./Biotech V. 14 73-75 Jan. 2005.*
Kondamudi, R. et al. Review Euphorbiaceae—A critical Review on Plant Tissue culture. Tropical and Subtropical Agroecosystems, 10 (2009): 313-335.*
Bhattacharyya, R. and Bhattacharya, S. 2001. high frequency invitro propagation of *Phyllanthus amarus* Schum. & Thonn. by shoot tip culture. Indian Journal Experimental Biology, 39: 1184-1187. (abstract).*
Quraishi, A. and Mishra, S. K. 1998. Micropropagation of nodal explants form adult trees of *Cleistanthus collinus*. Plant Cell Reports, 17: 430-433.*
Uchida, H. et al. Plant regeneration from inter node explants of *Euphorbia tirucalli*. Plant Biotechnology 21: 397-399.*
Villaluz, Z.A. 2006. Improvement of in vitro techniques for rapid meristem development and mass propagation of philippine Cassava (manihot esculenta crantz) Journal of Food Agriculture and Environment 4:220-224. (abstract).*
Gaydou et al., "Energy sources of plant origin in Madagascar: ethyl alcohol and seed oils",*Oleagineux*, 37(3):135-141 (1982) (English Abstract Only).
Staubman et al., "Esterase and lipase activity in *Jatropha curcas* L. Seeds", *J. Biotechnol.*, 75:117-126 (1999).
Sujatha et al., "Morphogenesis and plant regeneration from tissue cultures of *Jatropha curcas*", Plant Cell, Tissue & Organ Culture, 44:135-141 (1996).
Swarup, R., "Biotechnological interventions for production and plantation of improved quality of *Jatropha*", Dept. of Biotechnol. Gov. of India, presentation (Aug. 2004).
Weida et al., "Induction of callus from *Jatropha curcas* and rapid propagation", *Chinese J. Applied & Environ. Biol.*, 9(2):127-130 (2003) (English Abstract Only).

* cited by examiner

*Primary Examiner* — Wendy C. Haas
(74) *Attorney, Agent, or Firm* — Mintz Levin Cohn Ferris Glovsky and Popeo, P.C.; Ivor R. Elrifi; Christina K. Stock, Esq.

(57) ABSTRACT

The present invention relates to a commercially viable process for in vitro mass culture of *Jatropha curcas*. The process for in vitro mass culture of *Jatropha curcas* is simple, faster, and suitable for production of disease-free root tubers of uniform quality and employs media with a reduced concentration of phytohormones.

8 Claims, 4 Drawing Sheets
(4 of 4 Drawing Sheet(s) Filed in Color)

COMMERCIALLY VIABLE PROCESS FOR IN VITRO MASS CULTURE OF *JATROPHA CURCAS*

FIELD OF THE INVENTION

The present invention relates to methods for in vitro micropropagation of *Jatropha curcas*. The invention in particular relates to a commercially viable process for in vitro mass culture using media with a reduced concentration of phytohormones.

BACKGROUND INFORMATION

*Jatropha curcas*, belonging to the family of Euphorbiaceous, is a plant of Latin American origin, widely spread throughout the arid and semi-arid tropical regions of the world. *Jatropha* is a large genus comprising over 170 species. The most common species in India are *J. curcas, J. glandulifera, J. gossypifolia, J. multifida, J. nana, J. panduraefolia, J. villosa* and *J. podagrica*.

*J. curcas* is a small tree or shrub with smooth gray bark, which exudes whitish colored, watery, latex when cut. Normally, it grows between three and five meters in height, but can attain a height of up to eight or ten meters under favorable conditions. It is a drought-resistant plant, living up to 50 years and growing on marginal lands.

*J. curcas* has large green to pale green leaves, which are aligned alternate to sub-opposite. The leaves are three-five lobed with a spiral phyllotaxis. The petiole of the flowers ranges between 6-23 mm in length. The flowers are formed in hot seasons. Several crops are formed provided the soil is moisture is good and temperatures are high. In conditions where continuous growth occurs, an imbalance of pistillate or staminate flower production results in a higher number of female flowers. Fruits are produced in winter when the shrub is leafless. Each inflorescence yields a bunch of approximately 10 or more ovoid fruits. Three, bi-valved cocci are formed after the seeds mature and the fleshy exocarp dries. The seeds become mature when the capsule changes from green to yellow, after two to four months from fertilization. The blackish, thin-shelled seeds are oblong and resemble small castor seeds.

This plant has various medicinal uses especially in nutraceuticals, pharmaceutical, dermatological, and personal care products. The latex of *Jatropha curcas* has anticancer properties due to the presence of an alkaloid known as "jatrophine." The tender twigs are used for cleaning teeth. The juice of the leaf is used for external application for piles. The roots are used as an antidote for snake-bites. The seeds are used for antihelmithic purposes.

The bark yields a dark blue dye used for coloring cloth, fish net and lines.

Most of the *Jatropha* species are ornamental except for *J. curcas* and *J. glandulifera* which are oil-yielding species (as projected in presentation on "Biotechnological interventions for production and plantation of improved quality of *Jatropha*" by Dr. Renu Swarup, 2004). The seeds of these species contain semi-dry oil which has been found useful for medicinal and veterinary purposes (Gubitz et al., 1999 "Esterase and lipase activity of *Jatropha curcas* seeds J. Biotechnology October 8:75(2-3): 117-26).

The oil content is 25-30% in the seeds and 50-60% in the kernel. The oil contains 21% saturated fatty acids and 79% unsaturated fatty acids. *Jatropha* oil contains linolenic acid (C18:2) and oleic acid (C18:1) which together account for up to 80% of the oil composition. Palmitic acid (C16:0) and stearic acid (C18:0) are other fatty acids present in this oil.

The oil is non-edible, however it has the potential to provide a promising and commercially viable alternative to diesel oil as it has all the desirable physicochemical and performance characteristics as that of diesel. The plant *J. curcas* has lately attracted particular attention as a tropical energy plant. The seed oil can be used as a diesel engine fuel for it has characteristics close to those of fossil fuel diesel. Moreover, due to its non-toxic and biodegradable nature, *Jatropha* biodiesel meets the European EN 14214 standards of a pure and blended automotive fuel for diesel engines. *Jatropha curcas* seed yields approach 6-8 MT/ha with ca 37% oil. Such yield could produce the equivalent of 2100-2800 liters of fuel oil/ha, whose energy is equivalent to 19,800-26,400 kwh/ha (Gaydou, A. M., Menet, L., Ravelojaona, G., and Geneste, P. 1982. Vegetable energy sources in Madagascar: ethyl alcohol and oil seeds (French). Oleagineux 37(3):135-141).

Because of its very high saponification value and its ability to burn without emitting smoke, the oil of the seeds is commercially useful. For example, it is extensively used for making soaps.

Therefore, in view of the above, there is a need to provide method for micropropagation of *Jatropha curcas* which are economical and allow production on a commercial scale of uniform quality, true-to-type, disease-free plants.

Plant Tissue Culture

Micropropagation is the in vitro regeneration of plants from organs, tissues, cells or protoplast using techniques like tissue culture for developing true-to type resultant plants of a selected genotype. In general, tissue from a plant commonly known as an explant is isolated to create a sterile tissue culture of that species in vitro. A culture is initiated from an explant. Once a culture is stabilized and growing well in vitro, multiplication of the tissue or regeneration of entire plant can be carried out. Shoots (tips, nodes or internodes) and leaf pieces are commonly used but cultures can be generated from many different tissues. Juvenile tissues generally respond best. Besides the source of the explant, the chemical composition of the culture medium and the physical environment of cultures have been found to be of a great influence on the regeneration capacity, multiplication ratio, growth and development of new plants in the culture system. Therefore one needs to optimize these factors for each individual plant species.

Sujatha and Mukta ("Morphogenesis and Plant regeneration from tissue cultures of *Jatropha curcas*", Plant Cell Tissue & Organ Culture, 44(135-141)1996) have reported a method for the differentiation of adventitious shoots through callus derived from hypocotyl, petiole, and leaf explants of *J. curcas*. Weida Lu, Tang Lin, Yan Fang & Chen Fang (2003) ("Induction of callus from *Jatropha curcas* and rapid propagation," College of Life Science, Sichuan University Chengdu 610064, China) have reported induction of adventitious buds and regenerated shoots from epicotyl explants through callus.

All of the above studies focused on callus-mediated regeneration. Plant tissue regeneration through a callus stage is vulnerable to somaclonal variations and hence will not ensure true-to-type plants from elite mother plants. In addition, all of the above studies used non-meristem tissue, which is more likely to be infected with disease than meristem tissue. Therefore, there remains a need in the art for micropropagation methods that allow the production of true-to-type, disease-free plants.

SUMMARY OF THE INVENTION

The present invention provides for the first time the use of meristem tissue as an explant for direct organogenesis giving rise to true-to-type clones. Although Applicants do not wish to be bound by theory, they believe that the success of the present invention depends upon the use of meristem and a low concentration of phytohormones.

The invention provides methods for producing a true-to-type clone of a *Jatropha curcas* mother plant by culturing a meristematic explant of *Jatropha curcas* in media with phytohormones at a concentration from about 0.01 mg/L to about 10 mg/L and producing a true-to-type clone of a *Jatropha curcas* mother plant from said meristematic explant.

In preferred embodiments, the meristematic explant is from a shoot tip or a nodal bud. Preferably, the shoot tip has bud tissue. Preferably; this bud tissue is apical bud tissue.

In certain embodiments, the phytohormones are at concentration of 0.01 mg/L, 0.1 mg/L, 0.5 mg/L, 1 mg/L, 5 mg/L, or 10 mg/L. Preferably, the phytohormones are at a concentration from about 0.1 mg/L to about 0.3 mg/L.

The phytohormones used in the invention may be cytokinins, cytokinin-active urea derivatives, auxins, or gibberellins. Cytokinins that may be used in this invention include 6-aminopurine (adenine), 6-aminopurine hydrochloride, 6-aminopurine hemisulfate, 6-benzyl aminopurine (BAP), kinetin, zeatin, and N6-substituted derivatives. In preferred embodiments, the cytokinin is 6-benzyl aminopurine at a concentration from about 0.44 µM to about 2.22 µM and most preferably at about 0.44 µM. Cytokinin-active urea derivatives that may be used in this invention include thiadiziron, diphenylurea, and N-phenyl-N'-(4-pyridyl) urea. Auxins that may be used in this invention include naphthalene acetic acid, naphthaleneacetamide, naphthoxyacetic acid, indole acetic acid, indole butyric acid (IBA), 4-chlorophenoxyacetic acid, 2,4-dichlorophenoxyacetic acid (2,4-D), and 2,4,5-trichlorophenoxyacetic acid. Preferably, the auxin is indole butyric acid is at a concentration of about 4.9 µM.

Steps in in vitro mass culture can include selecting the healthy mother plants, isolating explants from a mother plant, cleaning, sterilizing the explants by primary and secondary sterilization, inoculating the explants on culture initiation medium having basal salts of MS medium to give multiple shoots, transferring the cultures to proliferation and elongation medium having basal salts of MS medium the same as the initiation medium, transferring the elongated shoots to rooting medium having basal salts of MS medium, subjecting in vitro grown plantlets to primary and secondary hardening, and transferring the hardened plantlets to fields.

In preferred embodiments of this invention, explants are selected from buds with shoot tips and nodal segments. In the most preferred embodiments the explant is the apical bud.

In the most preferred embodiments of the present invention the MS medium employed for culture initiation, proliferation and elongation, and rooting has a reduced phytohormone level, thereby rendering the process cost-effective.

Thus, the use of meristematic tissue as an explants and the use of very reduced concentrations of phytohormone, such as 0.44 µM-4.4 µM of 6-benzyl amino purine in proliferation and initiation medium, which can give 3-4 shoots per explants and high success rate during rooting and hardening, renders the present invention commercially viable for in vitro mass culture of *Jatropha curcas* for large-scale multiplication of true-to-type clones of elite variety plants.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

Definitions

Figure 1:
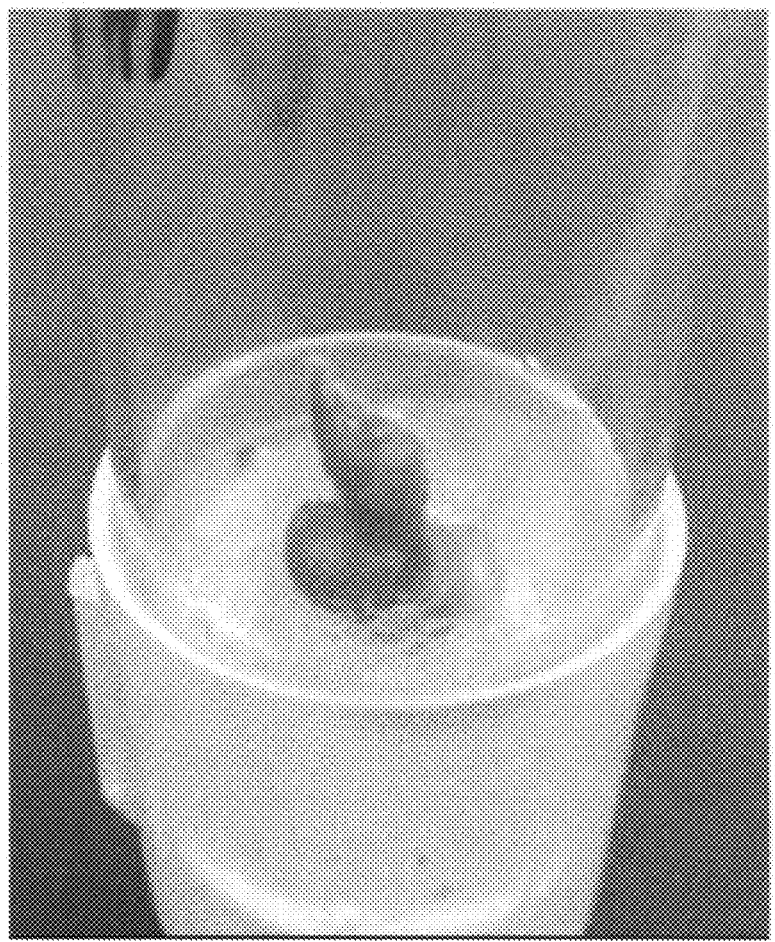
FIG. 1 shows the initiation of the apical bud of *Jatropha curcas*.
Figure 2:
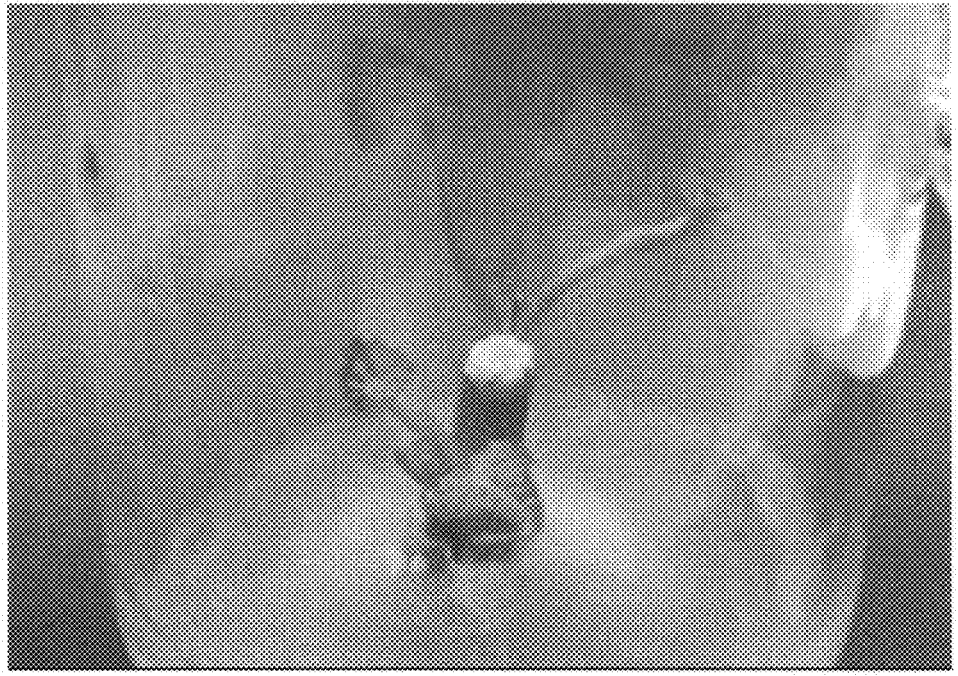
FIGS. 2 to 4 show *Jatropha curcas* cultures with multiple shoots from a single explant.
Figure 3:
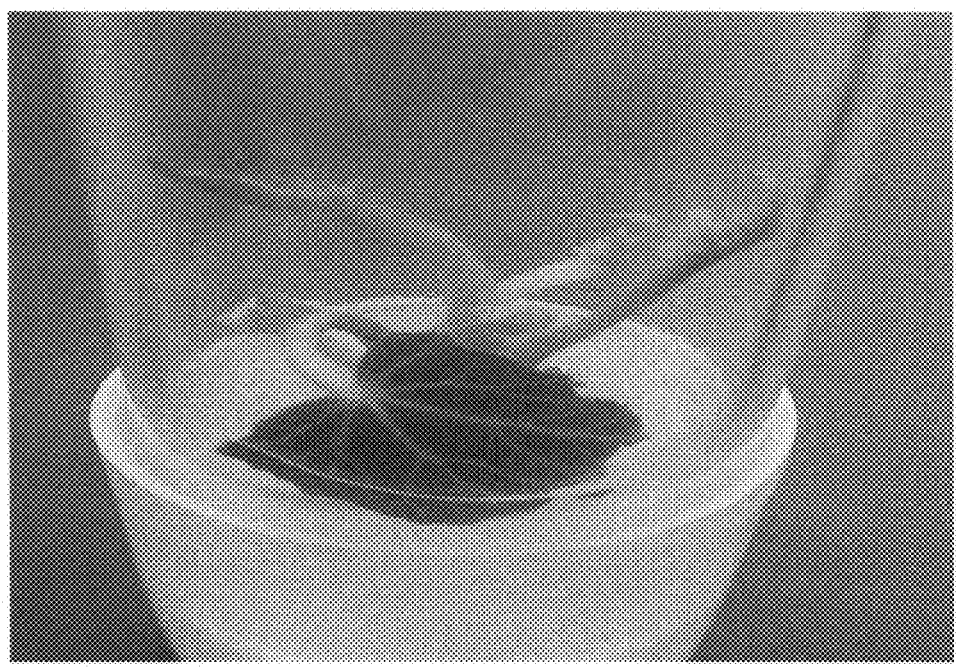
Figure 4:

"Micropropagation" refers to the in vitro regeneration of plants from organs, tissues, cells or protoplasts and the true-to-type propagation of a selected genotype using in vitro culture technique.

"Callus" refers to an unorganized or undifferentiated mass of proliferative cells produced either in culture or in nature.

"True-to type propagation" means that all characteristics present in mother plant will also be present in next generation, i.e., the plantlets will be the true type of the mother plant.

"Fungicide" means any chemical substance that destroys and inhibits the growth of fungi. "Insecticide" means any substance, synthetic or organic, which inhibits, kills, or destroys insects.

"MS" refers to Murashige and Skoog's medium.

"IBA" refers to Indole-3-butyric acid.

"FYM" refers to farm yard manure which can be like compost.

"M-45" refers to Dithane M-45.

"BAP" refers to 6-benzyl amino purine.

General

The present invention provides a commercially viable process for in vitro mass culture of *Jatropha curcas* to generate true-to-type clones of elite variety having the steps of using meristematic explants and culturing them in a media with a reduced concentration of phytohormones. In contrast to existing methods, the process allows the cultivation of true-to-type clones with a high success rate. Using this process, one can obtain multiple shoot ratios up to 1:3, rooting success rates up to 90%, hardening success rates up 70%, and field success rates up to 100%.

In some embodiments, the process has steps including, but not limited to, selecting the healthy mother plants, treating the mother plant, isolating the explants from an elite variety of mother plants, cleaning of the explants, sterilizing the explants by primary and secondary sterilization, inoculating the explants on culture initiation medium, transferring the cultures to proliferation and elongation medium, transferring the elongated shoots to rooting medium, subjecting in vitro grown plantlets to primary and secondary hardening, and transferring the hardened plantlets to fields.

Preparation of the Mother Plant

In certain embodiments, the mother plant from which the explants are harvested is subject to screening to identify healthy specimens and/or treatment to either maintain a disease-free state or to treat existing disease.

Health can be determined by assessing the plants for their size, weight, general growth, appearance, and absence of infection or contamination. *J. curcas* plants are commonly infected with "frogeye" (*Cercospera* spp.), insects of the order of Heteroptera and the golden flea beetle (*Podagrica* species).

Decontamination can be performed by spraying the plants with agents such as fungicides, insecticides, pesticides or the like. Preferred fungicides for the pretreatment of the mother plant include Bavistin™, Captan™, Dithane™, Thiram™, Thiovit™, or combinations thereof at a concentration of about 0.05% to 0.2%. Preferred insecticides for the pretreatment of the mother plant include, but are not limited to, Rogor™, Nuvacron, Fastac™, Ultracid™ 40-WP, Thiodane™ at a concentration of about 0.005% to 0.02%.

Explants

The present invention provides a method for efficient in vitro mass culture of *Jatropha curcas* using explants from meristematic tissue. Since meristematic cells are undifferentiated, the use of such tissue as an explant allows regeneration of true-to-type clones of the mother plants.

In preferred embodiments, shoot tip or nodal buds are used as explants. In the most preferred embodiments, the contemplated explant is shoot tip with bud tissue. Apical meristem bud tissue is particularly preferred, as it is an active part of the plant and relatively contamination free.

Preferably, the explant used in the present invention is selected from healthy, fresh, disease-free plants. The explants may be isolated from mother plants growing in various locations, both wild and cultivated.

Preparation of the Explants for Culture

Cleaning of Explants

In some embodiments, the explants are cleaned prior to inoculation in the media. Cleaning is performed using methods known to those of skill in the art, for example, by shaking explants in a mild detergent, such as Tween-20.

Sterilization of Explants

In other embodiments, the explants are sterilized prior to inoculation in the media. Sterilization can be performed using any method known to those of skill in the art, for example, by treatment with fungicide, a surface sterilizing agent, or combinations thereof. The explant may be subjected to a single round of sterilization or multiple rounds of sterilization.

For example, the explant may go through a primary sterilization step with the fungicide Bavistin and then go through a secondary sterilization with a surface sterilizing agent like sodium hypochlorite or mercuric chloride.

Culture of Explants

The present invention provides a method for efficient in vitro mass culture of *Jatropha curcas* using meristematic explants and culture in media with a reduced concentration of phytohormones.

Other aspects of the micropropagation process can be performed using methods known to those of skill in the art in plant tissue culture. Micropropagation typically involves the following steps:

1) culturing explants in initiation media to generate multiple shoots
2) transferring shoots to proliferation and elongation media
3) transferring the elongated shoots to rooting media
4) hardening the plantlets, and
5) transferring the hardened plantlets to fields.

The basal media used to culture *Jatropha* can be any of those already known in the field of the art for plant tissue culture, such as Murashige & Skoog, Gamborg's, Vacin & Went, White's, Schenk & Hildebrandt or the like.

Basal media can also be supplemented with various carbon sources. The carbon source may be sucrose or glucose, typically, at a concentration of about 2-5%. The carbon source may also be sugar alcohol like myo-inositol, typically, at a concentration of about 50-500 mg per liter.

In some embodiments, the basal media will include gelling agents such as agar, alginic acid, carrageenan, gellangum. Typical concentrations are 0.5-1%.

In one embodiment, the initiation medium is Murashige & Skoog medium with full strength of the basal nutrients with a reduced concentration of phytohormones, such as 6-benzyl amino purine (BAP) in the range of 0.44 µM-2.22 µM.

In some embodiments, the proliferation and shoot elongation medium and rooting medium have the same level of nutrients and phytohormones as the initiation medium. In other embodiments, the compositions are similar but not precisely the same.

Phytohormones in Media

The present invention provides for a method where meristematic explants are grown in media containing a reduced concentration of phytohormones.

The phytohormones used the media can be any phytohormone that will affect growth in the desired manner during different stages of tissue culture. Examples of suitable phytohormones include natural or synthetic auxin, cytokinin, gibberellin, or cytokinin-active urea derivatives.

The cytokinins used can include, but are not limited to, 6-aminopurine(adenine), 6-aminopurine hydrochloride, 6-aminopurine hemisulfate, 6-benzyl aminopurine (BAP), kinetin, zeatin, $N_6$-substituted derivatives, or derivatives of these compounds. Preferred cytokinin-active urea derivatives include, but are not limited to, thiadiziron, diphenylurea, N-phenyl-N'-(4-pyridyl)urea or their derivatives.

The auxins used can include, but are not limited to, naphthalene acetic acid, naphthaleneacetamide, naphthoxyacetic acid, indole acetic acid, indole butyric acid (IBA), 4-chlorophenoxyacetic acid, 2,4-dichlorophenoxyacetic Acid (2,4-D), 2,4,5-trichlorophenoxyacetic acid, or the like and their derivatives.

The phytohormone may be used singly or in combination with two or more other phytohormones.

The concentration of the phytohormone present in the media will be reduced as compared to that typically used to culture explants. The exact concentration used will depend on the stage of the method of the invention. The present invention provides that concentration is between 0.01 mg per liter to 10 mg per liter, such as 0.1, 0.5, 1, or 5 mg/L. In preferred embodiments, there is a low level of cytokinin and auxin in the media, for example, between 0.1 mg and 0.3 mg/L.

In one embodiment of this invention, a low level of cytokinin is used in the initiation and proliferation/elongation media while a low level of auxin is used in the rooting media.

In certain embodiments, the proliferation/elongation media also contains adenine sulphate, glutamine and activated charcoal.

Culture Conditions

In certain embodiments, the culture conditions (i.e., light cycle, light intensity, media, temperature, relative humidity) are the same throughout the initiation, proliferation and elongation, and rooting stages. Subculturing is performed as necessary; preferably, every 3 to 4 weeks.

Once well-formed roots are obtained, plantlets can be hardened on soil, sand, moss, charcoal or other media either alone or in combination in defined ratio. The plantlets can then be transferred to the fields by direct sowing or transplanting of the cuttings.

All references cited herein are hereby incorporated by reference.

The invention will be better understood by reference to the following Example.

EXAMPLE

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Selection of Explant

The shoots of a healthy elite mother plant of *Jatropha curcas* from the field were collected. Shoots were thoroughly washed under running water to remove dust adhering to the shoot.

Cleaning of the Explant

All pieces were separately cleaned with a 0.5% Tween-20 solution with intermittent shaking for 5 minutes and then washed thoroughly with demineralized water.

Sterilization of the Explant

Cleaned explants were subjected to primary sterilization by treating the explants with a solution containing 0.1% Bavistin™ for 5 minutes and then rinsing with sterile water. The explants were then subjected to secondary sterilization in a laminar flow bench by treating with 0.5% sodium hypochlorite for 5 minutes and rinsing with autoclaved distilled water repeatedly.

Preparation of the Explant for Inoculation

The explant was trimmed without damaging the apical and axillary meristem to isolate the meristematic tissue.

To avoid the contamination and the resultant loss of valuable cultures, each explant was washed and treated separately.

Inoculation and Proliferation/Elongation (FIGS. 1, 2, 3, 4)

The sterilized explants were inoculated in Murashige & Skoog Basal Medium with 0.44 μM 6-benzyl amino purine. The explants were cultured under the following conditions: an initial photoperiod of 16 hours under 2000 lux light intensity followed by 8 hours dark period at 25° C. temperature and 60% RH. After multiple shoots were generated, they were isolated and transferred into proliferation and elongation media with the same composition as the initiation medium. The multiple shoot ratio obtained was around 1:3. The elongated shoots were subcultured at a regular interval of about 4 weeks.

Figure 5:
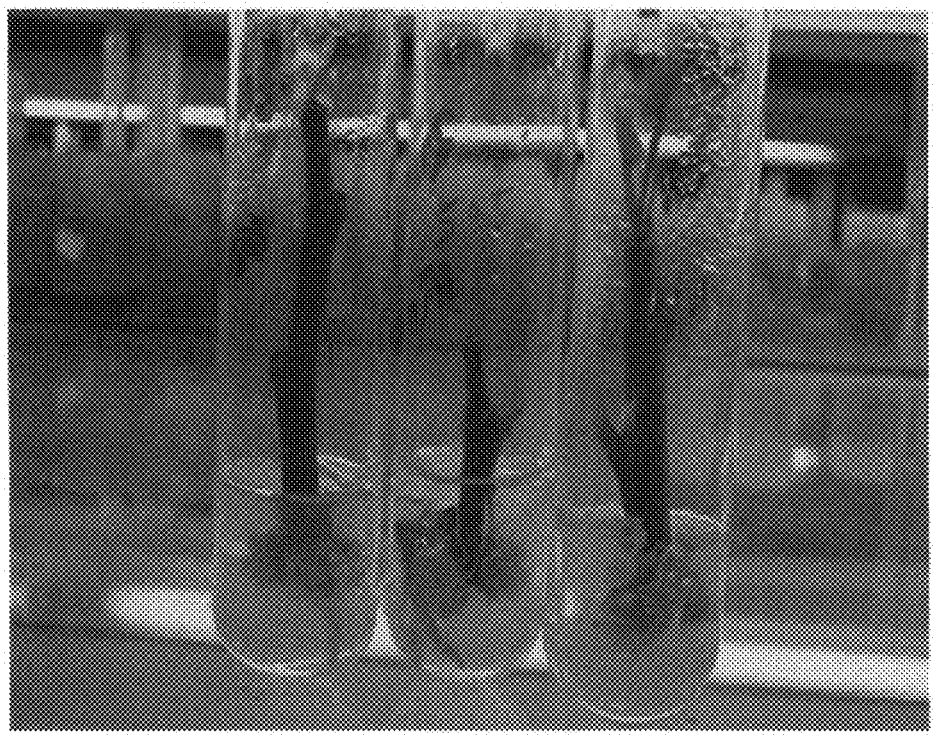
FIG. 5 shows *Jatropha curcas* shoots with roots.

Transferring to Rooting Medium (FIG. 5)

The healthy elongated shoots were transferred to rooting medium composed of half strength Murashige & Skoog Basal Medium with reduced concentration of auxin, 4.9 μM IBA, which allowed the shoots to grow to give well-formed roots.

Hardening Protocol for *Jatropha* Plantlets in Greenhouse

Figure 6:
FIG. 6 shows *Jatropha curcas* plantlets in greenhouse during the hardening step.

Primary Hardening (FIG. 6)

The steps involved are described below:
1. The plantlets raised in vitro were washed in tap water and then dipped in 1% Bavistin for 10 minutes.
2. They were then planted in portrays filled with FYM and soil (1:1) treated with 1% M-45 solution.
3. These portrays were then kept under polytunnels for 20 days, where a temperature of 23 to 28° C. and a relative humidity of 70% to 80% was maintained.
4. After 20 days, the plants were removed from polytunnels and kept at a temperature of 25 to 30° C. and a relative humidity of 60% for 20 days Secondary Hardening The steps involved are described below:
1. The plants were shifted in polybags with a potting mixture consisting of FYM and soil in a 1:1 ratio.
2. The plants were irrigated every three days.
3. After two months, the plants were ready to be dispatched to the field.

Thus, while we have described fundamental novel features of the invention, it will be understood that various omissions and substitutions and changes in the form and details may be possible without departing from the spirit of the invention. For example, it is expressly intended that all combinations of those elements and/or methods steps, which perform substantially the same function in substantially the same way to achieve the same results, be within the scope of the invention

The invention claimed is:

1. A method for producing a true-to-type clone of a *Jatropha curcas* mother plant comprising culturing a meristematic explant of *Jatropha curcas* in media with phytohormones at a concentration from 0.01 mg/L to 0.3 mg/L, wherein said phytohormones are cytokinins, and producing a true-to-type clone of a *Jatropha curcas* mother plant from said meristematic explant.

2. The method of claim 1, wherein said meristematic explant is from a shoot tip or a nodal bud.

3. The method of claim 2, wherein said meristematic explant is from a shoot tip.

4. The method of claim 3, wherein said shoot tip comprises bud tissue.

5. The method of claim 4, wherein said bud tissue is apical bud tissue.

6. The method of claim 1, wherein said phytohormones are at concentration selected from the group consisting of 0.01 mg/L, 0.1 mg/L, and 0.3 mg/L.

7. The method of claim 1, wherein said cytokinin is 6-benzyl aminopurine.

8. The method of claim 7, wherein said 6-benzyl aminopurine is at a concentration of 0.44 μM.

\* \* \* \* \*